(12) United States Patent
Yamada et al.

(10) Patent No.: US 10,761,051 B2
(45) Date of Patent: Sep. 1, 2020

(54) MOLECULAR DETECTION APPARATUS AND MOLECULAR DETECTION METHOD

(71) Applicant: KABUSHIKI KAISHA TOSHIBA, Minato-ku (JP)

(72) Inventors: Ko Yamada, Yokohama (JP); Hirohisa Miyamoto, Kamakura (JP); Reiko Yoshimura, Kawasaki (JP); Hiroko Nakamura, Yokohama (JP); Mitsuhiro Oki, Kawasaki (JP); Yasushi Shinjo, Kawasaki (JP); Masaki Atsuta, Yokosuka (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 301 days.

(21) Appl. No.: 15/912,678

(22) Filed: Mar. 6, 2018

(65) Prior Publication Data

US 2019/0086359 A1   Mar. 21, 2019

(30) Foreign Application Priority Data

Sep. 19, 2017   (JP) .................................. 2017-178635

(51) Int. Cl.
*G01N 27/414*   (2006.01)
*G01N 33/00*    (2006.01)
*G01N 27/68*    (2006.01)

(52) U.S. Cl.
CPC ..... *G01N 27/4141* (2013.01); *G01N 27/4146* (2013.01); *G01N 27/68* (2013.01); *G01N 33/0047* (2013.01)

(58) Field of Classification Search
CPC ............. G01N 27/414; G01N 27/4141; G01N 27/4146; G01N 21/766
See application file for complete search history.

(56) References Cited

U.S. PATENT DOCUMENTS 6,883,364 B2 * 4/2005 Sunshine ........... G01N 33/0009
                                                  73/23.34
8,993,700 B2 * 3/2015 Buvat ................ G01N 33/0037
                                                  526/266

(Continued)

FOREIGN PATENT DOCUMENTS

JP          3692342      9/2005
JP       2008-216083     9/2008

(Continued)

OTHER PUBLICATIONS

Kybert et al., "Scalable arrays for chemical vapor sensors based on DNA-decorated graphene," Nano Research 2014, 7(1):95-103 (Year: 2014).*

(Continued)

*Primary Examiner* — Alexander S Noguerola
(74) *Attorney, Agent, or Firm* — Oblon, McClelland, Maier & Neustadt, L.L.P.

(57) ABSTRACT

A molecular detection apparatus according to an arrangement includes: a collection unit collecting a detection target gas containing a molecule to be detected; a detector including a detection cell that has an organic probe provided in a sensor unit, the organic probe capturing the collected molecule, and a discriminator discriminating the molecule by a detection signal generated by the molecule being captured by the organic probe of the detection cell. The detection cell has the organic probe including a dicyanovinyl structure or a coumarin structure.

12 Claims, 9 Drawing Sheets

(56) References Cited

U.S. PATENT DOCUMENTS

| | | | |
|---|---|---|---|
| 2003/0143119 A1* | 7/2003 | Schwartz | G01N 21/643 422/82.08 |
| 2012/0171093 A1 | 7/2012 | Swager et al. | |
| 2012/0303305 A1 | 11/2012 | Bergqvist et al. | |
| 2013/0115705 A1 | 5/2013 | Patolsky et al. | |
| 2016/0013428 A1 | 1/2016 | Takimiya et al. | |
| 2016/0379814 A1 | 12/2016 | Yamada et al. | |
| 2017/0350854 A1 | 12/2017 | Yamada et al. | |
| 2018/0080911 A1 | 3/2018 | Yamada et al. | |

FOREIGN PATENT DOCUMENTS

| | | |
|---|---|---|
| JP | 2010-019688 | 1/2010 |
| JP | 2010-025719 | 2/2010 |
| JP | 2010-038569 | 2/2010 |
| JP | 2010-038840 | 2/2010 |
| JP | 2010-139269 | 6/2010 |
| JP | 2011-080798 | 4/2011 |
| JP | 2012-247189 | 12/2012 |
| JP | 2013-513810 | 4/2013 |
| JP | 2013-529308 | 7/2013 |
| JP | 2014-505580 | 3/2014 |
| JP | 2016-047777 | 4/2016 |
| WO | WO 2014/133100 A1 | 9/2014 |
| WO | WO 2015/136695 A1 | 9/2015 |
| WO | WO 2017/025996 A1 | 2/2017 |
| WO | WO 2017/042851 A1 | 3/2017 |

OTHER PUBLICATIONS

Jiang-Fei Xu, et al., "A colormetric and fluorometric dual-modal chemosensor for cyanide in water," Sensors and Actuators B: Chemical, vol. 168, 2012, pp. 14-19.

Gyeong Jin Park, et al., "A naked-eye chemosensor for simultaneous detection of iron and copper ions and its copper complex for colorimetric/fluorescent sensing of cyanide," Sensors and Actuators B: Chemical, vol. 229, 2016, pp. 257-271.

* cited by examiner

[ORGANIC COMPOUND 1A]   [ORGANIC COMPOUND 1B]   [ORGANIC COMPOUND 1C]

[ORGANIC COMPOUND 2A]

[ORGANIC COMPOUND 2B]

[ORGANIC COMPOUND 3A]

[ORGANIC COMPOUND 3B]

MOLECULAR DETECTION APPARATUS AND MOLECULAR DETECTION METHOD

CROSS-REFERENCE TO RELATED APPLICATION

This application is based upon and claims the benefit of priority from Japanese Patent Application No. 2017-178635, filed on Sep. 19, 2017; the entire contents of which are incorporated herein by reference.

FIELD

Embodiments described herein generally relate to a molecular detection apparatus and a molecular detection method.

BACKGROUND

A water heater or the like for household use is provided with an apparatus that detects carbon monoxide generated when incomplete combustion occurs and notifies the risk thereof at an early stage. Such a gas component considerably affects a human body. According to the guidelines from LP gas safety committee, it is set that a carbon monoxide concentration of approximately 200 ppm (parts per million) causes headaches. Although various methods have been known as a method of detecting a gas component having a relatively higher concentration, the detection methods have been limited for detecting the gas component having a concentration in the order of ppb (parts per billion) to ppt (parts per trillion), which corresponds to an extremely low concentration.

At a disaster site or a site at which an act of terrorism occurs or the like, it has been desired to sense the risk in advance by detecting an extremely small amount of the gas component. The gas component having an extremely low concentration is often detected by use of large equipment in research facilities. In this case, a large sized installation type apparatus, which is expensive and has large weight and volume, such as a gas chromatography or a mass spectrometer, is required. Under such circumstances, it has been required to provide an apparatus that is capable of detecting the gas component having the extremely low concentration in real time, in other words, an apparatus that has smaller weight and volume and better portability and enables selective and higher sensitive detection of the gas component having the extremely low concentration in the order of ppt to ppb.

Incidentally, as the gas component required to be detected at the extremely low concentration, an explosive component released from explosives used in the act of terrorism can be cited, for example. The explosives release a slight amount of explosive component even in a sealed state, it is general, on a site such as an airport or the like, to find such an explosive component by a trained police dog or the like. Though such a method is highly effective from a standpoint of deterrence, an approach by use of an animal is costly and, in addition, has difficulty in securing a constant accuracy. Other than the explosives, cyanide, which is comparatively easily available, is imagined to be gasified and used. The cyanide is used in a process of abstracting metal by treatment of a mineral as well as in a plating process or the like, comparatively easily available and having quite high toxicity, and it is said that exposure to its vapor having a concentration of about several ppm influences a human life. Thus, it is desired that a cyan-based gas (a volatile component gas or a cracked gas of cyanide) is detected at a lowest possible concentration for the sake of speedy evacuation, for a highly public facility such as a station or an airport, for example.

As a detection element for a gas component having a low concentration, for example, an element has been known which has a conductive layer in which a surface of a carbon nanostructure or graphene is surface modified with an organic substance or the like that selectively reacts with or adsorbs a specific substance and measures a potential difference or the like that changes depending on the gas component having adhered to the surface of a conductive layer. With regard to the detection element as above, the kinds themselves of the organic substance that functions as a detection probe are limited, and an organic substance enabling a sufficient interaction with a cyan-based gas (a volatile component gas or a cracked gas of the cyanide) has not been found. Under the circumstances, there are strongly demanded a molecular detection apparatus and a molecular detection method which enable detection of a cyan-based gas at a lowest possible concentration and which serve as an alternative to a method which has difficulty in securing a constant accuracy, such as a detection method using an animal.

DETAILED DESCRIPTION

According to the embodiments of the present invention, there is provided a molecular detection apparatus that includes: a collection unit collecting a detection target gas containing a molecule to be detected; a detector comprising a detection cell which has a sensor unit and an organic probe provided in the sensor unit, the organic probe including a dicyanovinyl structure or a coumarin structure, and capturing the molecule collected in the collection unit; and a discriminator discriminating the molecule based on a detection signal generated from the sensor unit by the molecule being captured by the organic probe of the detection cell.

Hereinafter, there will be described a molecular detection apparatus and a molecular detection method according to embodiments with reference to the drawings. In each embodiment, substantially the same constituent elements are denoted by the same reference signs and a description thereof will be omitted in some cases. The drawings are schematic, and a relation of a thickness and a planar dimension of each part, a thickness ratio among parts, and so on may differ from actual ones.

Figure 1:
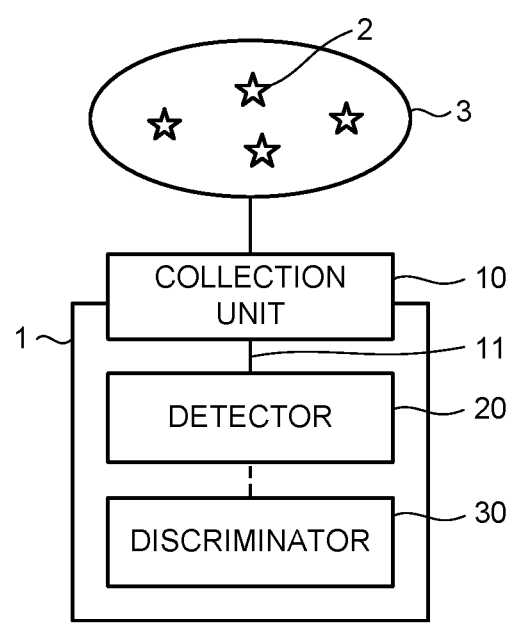
FIG. 1 is a block diagram illustrating a molecular detection apparatus of an embodiment.

FIG. 1 is a block diagram illustrating a molecular detection apparatus according to the embodiment. A molecular detection apparatus 1 illustrated in FIG. 1 is, for example, an apparatus that detects, from a detection target gas 3 containing molecules to be detected (substances to be detected) 2 generated from a gas generation source, the molecule to be detected 2, and includes a collection unit 10, a detector (molecular detector) 20, and a discriminator 30. The detection target gas 3 containing the molecules to be detected 2 is first collected by the collection unit 10 in the molecular detection apparatus 1. The collection unit 10 has a collection port for the detection target gas 3 and is connected to the detector 20 via a gas flow channel 11. The collection unit 10 may include a filter for removing impurities such as fine particles contained in the detection target gas 3.

Figure 2:
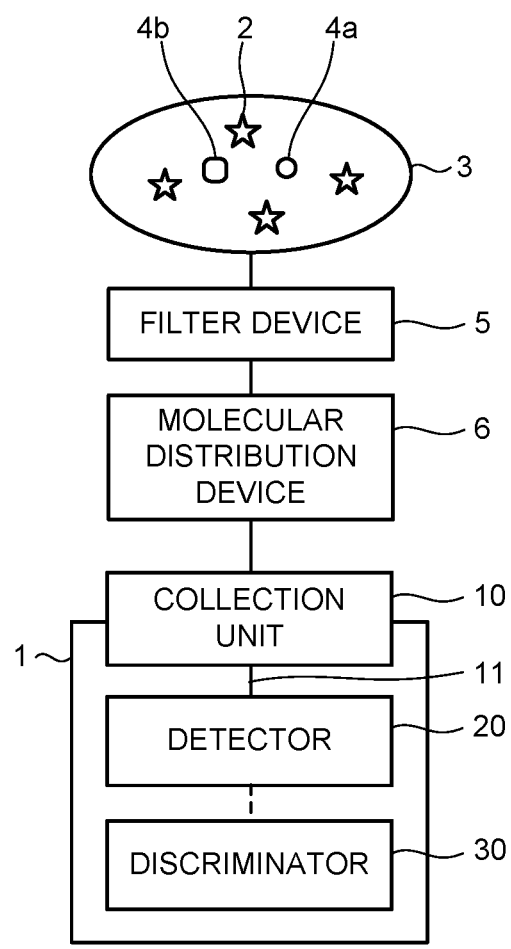
FIG. 2 is a block diagram illustrating a modification example of the molecular detection apparatus illustrated in FIG. 1.

The detection target gas 3 sometimes contains, as impurities, substances having a molecular weight, a molecular structure or the like similar to those of the molecules to be detected 2. As illustrated in FIG. 2, the molecules to be detected 2 drifting in the air often exist in a state where the molecules to be detected 2 are mixed with various foreign substances 4 (4a and 4b) such as odor components and fine particles. From those perspectives, as illustrated in FIG. 2, the detection target gas 3 may be sent to the molecular detection apparatus 1 after being preprocessed by a filter device 5, a molecular distribution device 6, and the like beforehand.

For the filter device 5 out of the devices of preprocess, a generally-used moderate-to-high performance filter or the like is used. The filter device 5 removes particulate substances such as fine particles contained in the detection target gas 3. The detection target gas 3, from which the particulate substances are removed in the filter device 5, is then sent to the molecular distribution device 6. As the molecular distribution device 6, there can be cited an apparatus that ionizes the detection target gas 3 to form an ionized substance group, applies voltage to the ionized substance group to allow the ionized substance group to fly at a speed proportional to the mass thereof, and separates an ionized substance of the molecule to be detected 2 from the ionized substance group by using a flight speed based on the difference in mass and a time of flight based on the flight speed. As the molecular distribution device 6 as above, a device including an ionization unit, a voltage application unit, and a time-of-flight separation unit is used.

Figure 3:
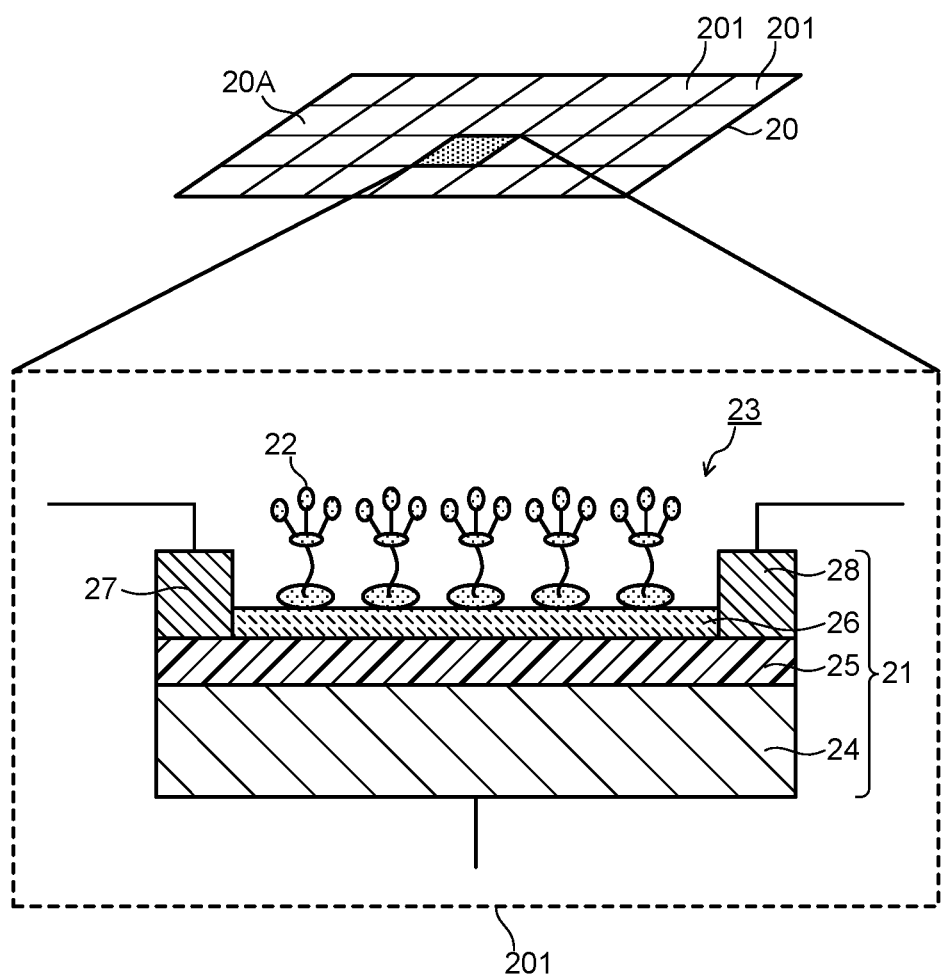
FIG. 3 is a view illustrating a configuration of a detector of the embodiment.

The detection target gas 3 containing the molecules to be detected 2 is collected by the collection unit 10 directly, or after being preprocessed by the devices such as the filter device 5 and the molecular distribution device 6. The molecules to be detected 2 collected by the collection unit 10 are sent to the detector 20 via a gas flow channel 11. The detector 20 includes a detection surface 20A sectioned into a plurality of detection cells 201 as illustrated in FIG. 3. The detection surface 20A of the detector 20 is disposed to face an outlet port (not shown) for the molecule to be detected 2 of the gas flow path 11. The plurality of detection cells 201 each include a detection element 23 having a sensor unit 21 and organic probes 22 provided in the sensor unit 21. FIG. 3 illustrates the detection element 23 where a graphene field effect transistor (GFET) is used for the sensor unit 21.

The GFET serving as the sensor unit 21 includes a semiconductor substrate 24 that functions as a gate electrode, an insulating film 25 provided as a gate insulating layer on the semiconductor substrate 24, a graphene layer 26 provided as a channel on the insulating film 25, a source electrode 27 provided at one end of the graphene layer 26, and a drain electrode 28 provided at the other end of the graphene layer 26. The organic probes 22 are provided on the graphene layer 26. The molecule to be detected 2 introduced to the detector 20 is captured by the organic probe 22 on the graphene layer 26. An electron transfers from the molecule to be detected 2 captured by the organic probe 22 to the GFET 21, thereby electrical detection is carried out. In this way, the target molecule to be detected 2 is detected.

Since an organic matter constituting the organic probe 22 has a property of dissolving in a solvent, the organic probe 22 can be installed at the graphene layer 26 by applying a solution obtained by dissolving the organic matter in a solvent. In order to easily obtain an interaction with graphene, the organic probe 22 preferably has a portion having such a structure as a pyrene ring. A molecule having such a structure as the pyrene ring interacts with a hexagonally shaped π electron system constituted by carbon of the graphene, and forms an interaction state of what is called a π-π stacking. Low-concentration probe molecules are dissolved in a solvent to be applied to the graphene, whereby the π-π stacking is formed between the pyrene ring and the graphene and the probe molecules are aligned on the graphene to then be fixed. By using such a self-alignment action, the organic probe 22 can be installed on the graphene layer 26. Organic compounds constituting the organic probe 22 will be described in detail later.

When the molecules to be detected 2 are captured by the organic probes 22 provided on the graphene layer 26, an output from the GFET 21 changes. In a case of the graphene of a single layer, there is zero gap, and thus, the source electrode 27 and the drain electrode 28 are continuously electrified normally. When the number of graphene layers increases to two or three layers, a band gap is generated, but such a band gap in an actual system is relatively smaller than that considered from a strict theoretical value. When the gate insulating layer 25 has a dielectric constant approximately similar to that of a silicon oxide film, the source electrode 27 and the drain electrode 28 are often continuously electrified. Thus, the graphene layer 26 may be constituted by a stack composed of about five graphene layers or less as well as the single layer structure of graphene.

The molecule to be detected 2 flying to the vicinity of the organic probe 22 is attracted to the organic probe 22 by hydrogen bonding force or the like, or comes into contact with the organic probe 22 in some cases. When the contact with the molecule to be detected 2 occurs, an interchange of electrons occurs between the molecule to be detected 2 and the organic probe 22, and the organic probe 22 transmits an electrical change to the graphene layer 26 being in contact therewith. The electrical change transmitted from the organic probe 22 to the graphene layer 26 disturbs the flow of electricity between the source electrode 27 and the drain electrode 28, and thus the GFET 21 functions as a sensor.

Figure 4:
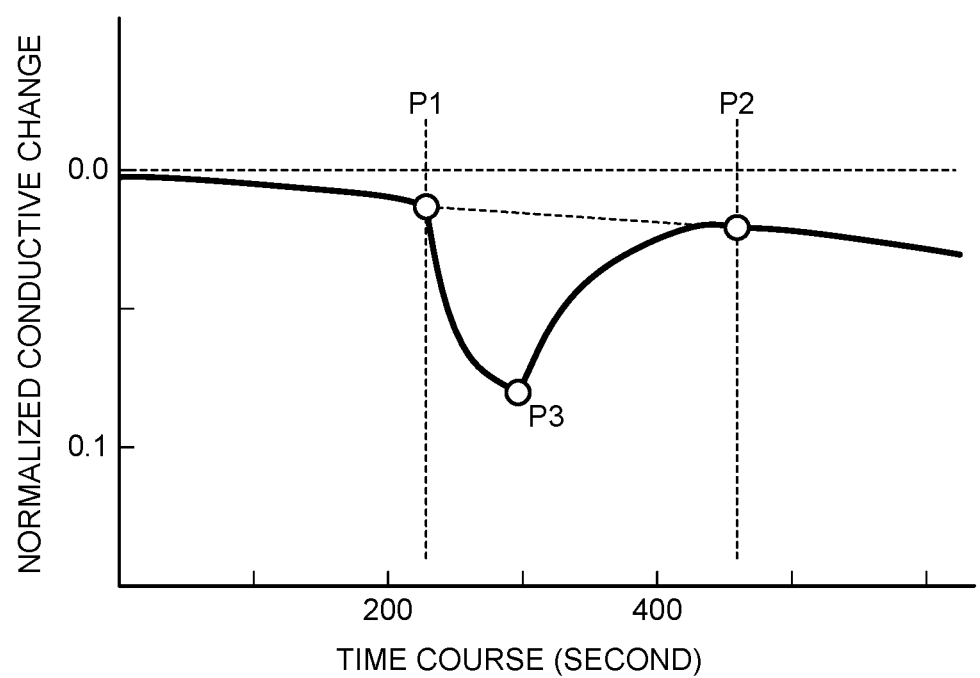
FIG. 4 is a graph illustrating an example of a detected waveform of a molecule to be detected by a molecular detection apparatus of an example.

With the GFET 21 using the graphene layer 26 as a channel, even an extremely slight electrical change appears significantly as an output. As a result, it is possible to constitute the highly sensitive detection element 23. The sensor using the GFET 21 has a tendency that electric current flows between the source electrode 27 and the drain electrode 28 without application of voltage to the gate electrode 24 because the graphene has a property as a zero-gap semiconductor. Thus, the GFET 21 functions as a sensor as it is. However, normally, electric current is made to flow between the source electrode 27 and the drain electrode 28 in a state where voltage to the gate electrode 24 is applied, and an electrical change of the gate electrode 24 when the organic probe 22 captures the molecule to be detected 2 is observed. FIG. 4 illustrates an example of a detected waveform of the molecule to be detected 2 by the molecular detection apparatus 1. When the organic probe 22 captures the molecule to be detected 2, a change illustrated in FIG. 4 appears in the detected waveform. There are various methods of converting the detected waveform into a signal strength, and for example, a value calculated from an area of P1 and P2, and P3 being a tip of a peak in FIG. 4, is set as the strength. However, the method is not necessarily limited to the above method.

In the detection of the molecule to be detected 2 performed by the above-described detection element 23, as the transfer of electrons from the molecule to be detected 2 that is captured by the organic probe 22 to the GFET 21 is higher, the function as the sensor is further increased. The sensor using the GFET 21 is regarded as the most sensitive FET sensor, and can improve a sensitivity about three times as compared with a sensor using a carbon nanotube. Thus, using the detection element 23 in which the GFET 21 and the organic probe 22 are combined enables higher sensitive detection of the molecule to be detected 2.

Figure 5:
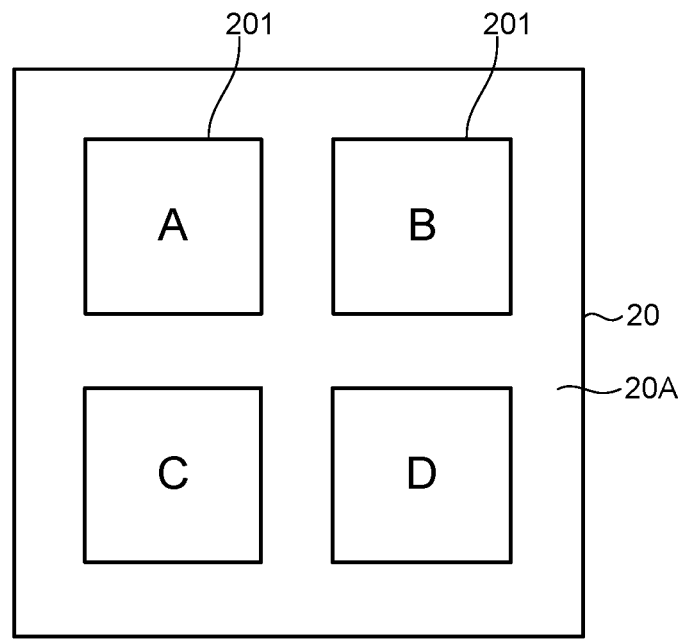
FIG. 5 is a diagram illustrating an example of a plurality of detection cells by a molecular detection apparatus of the embodiment.

FIG. 5 illustrates the detection surface 20A on which the plurality of detection cells 201 are arranged in a grid pattern (an array pattern), but arrangement is not necessarily limited to the above. The plurality of detection cells 201 may be arranged linearly. At least some of the organic probes 22 among the probes 22 respectively provided at the graphene layers 26 of the plurality of detection cells 201 are different in working strength (bond strength) with the molecule to be detected 2. That is, the plurality of detection cells 201 include a plurality of the organic probes 22 different in bond strength with the molecule to be detected 2. All the organic probes 22 may be different in bond strength with the molecule to be detected 2, or some of the organic probes 22 may be different in bond strength with the molecule to be detected 2.

Figure 6:
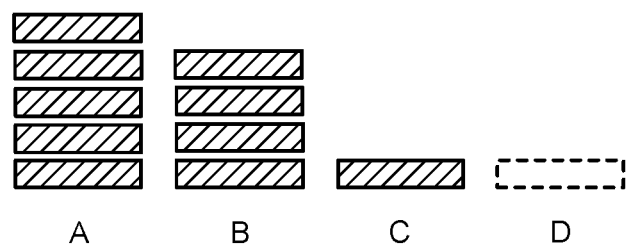
FIG. 6 is a diagram illustrating an example of a detection result of molecules to be detected, by the plurality of detection cells illustrated in FIG. 5.
Figure 7:
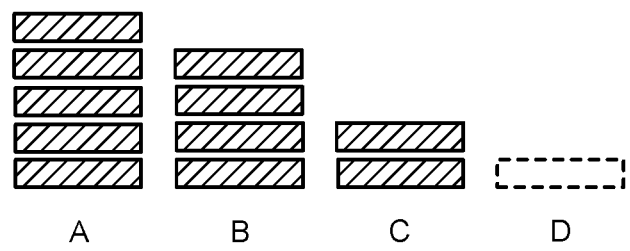
FIG. 7 is a diagram illustrating another example of the detection result of the molecules to be detected, by the plurality of detection cells illustrated in FIG. 5.

FIG. 5 illustrates a grid-shaped sensor in which the detection surface 20A of the detector 20 is sectioned into four detection cells 201, that is, a detection cell A, a detection cell B, a detection cell C, and a detection cell D. At least in some of the detection cells A to D, different kinds of organic probes 22, that is, the plurality of organic probes 22 different in bond strength with the molecule to be detected 2 are provided. The plurality of organic probes 22 each have an interaction with the molecule to be detected 2, but are different in bond strength with the molecule to be detected 2, and thus detection signals having different strengths are outputted. FIG. 6 and FIG. 7 illustrate examples of detection signals by the detection cells A to D.

The detection signals from the detection cells A to D have different signal strengths respectively, depending on the bond strength of the organic probe 22 with the molecule to be detected 2.

The signals detected in the detection cells A to D are sent to the discriminator 30 to be signal-processed. The discriminator 30 converts the detection signals from the detection cells A to D into strengths and analyzes signal patterns based on strength differences of these detection signals (four detection signal patterns illustrated in FIG. 6 and FIG. 7). The discriminator 30 stores therein signal patterns according to a substance to be detected and compares these signal patterns with the signal patterns detected in the detection cells A to D, to thereby discriminate the molecule to be detected 2 detected in the detector 20. Such a signal processing is called a pattern recognition method here. The pattern recognition method enables detection and discrimination of the molecule to be detected 2 by signal patterns peculiar to a substance to be detected like a dactyloscopy, for example. Accordingly, selective and higher sensitive detection of a gas component (the molecule to be detected 2) having an extremely low concentration in the order of ppt to ppb is enabled.

Application of the above-described pattern recognition method enables selective and higher sensitive detection and discrimination of the molecule to be detected 2 even when impurities are mixed in the detection target gas 3 that is introduced to the detector 20. For example, in a case where the molecule to be detected 2 is dimethyl methylphosphonate (DMMP, molecular weight: 124), which is a typical material for a toxic organophosphorus compound, there exist agricultural chemicals containing phosphoric acid such as dichlorvos having a similar chemical structure and organophosphorus pesticides, which are used often, such as malathion, chlorpyrifos, and diazinon. In order to prevent an erroneous detection of these substances, discrimination by such signal patterns as illustrated in FIG. 6 and FIG. 7 is effective. Since the signal patterns detected in the detection cells A to D are different according to the above-described respective substances, application of the pattern recognition method enables selective and higher sensitive detection of the detection target substance even when an impurity that has a similar molecular weight and a similar constituent element is mixed.

Figure 8:
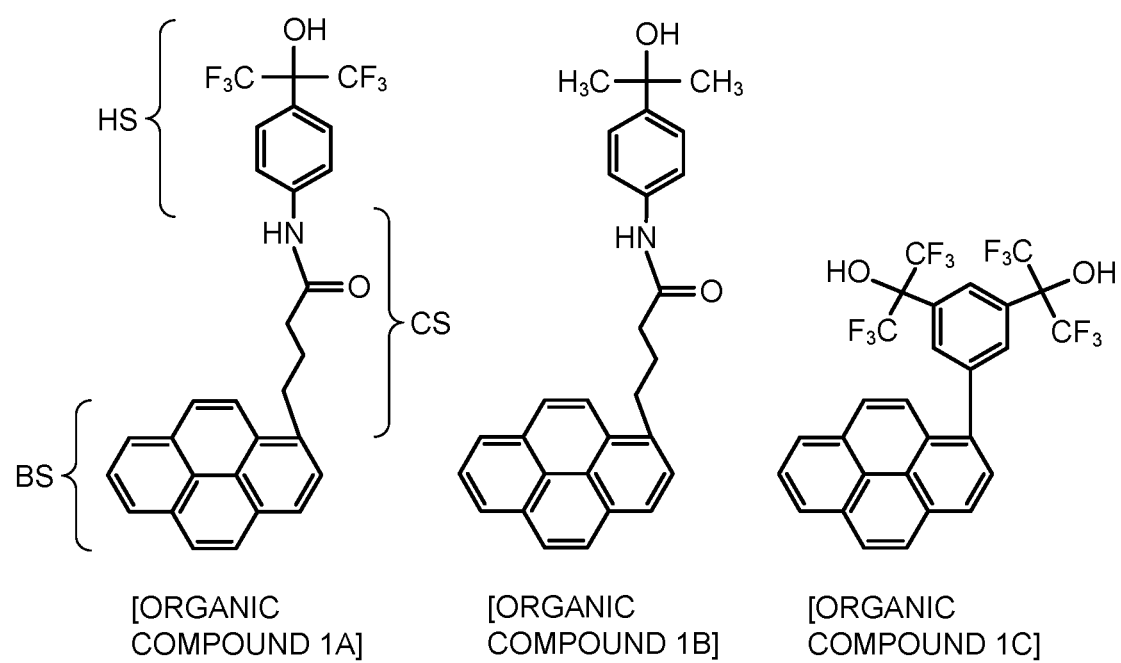
FIG. 8 is a diagram illustrating a first example of organic compounds used for organic probes in the molecular detection apparatus of the embodiment.

Next, there is described in detail the organic probe 22 to be used for the detection cell 201 of the molecular detection apparatus 1 according to the embodiment. An organic compound constituting the organic probe 22 has a hydroxy group (—OH), for example, as a reactive group to the molecule to be detected 2. However, the reactive group (—OH) alone hardly reacts with the gas component. Thus, for the purpose of enhancing a hydrogen bonding property or the like, an organic compound having a structure in which a circumference of the reactive group (—OH) is fluorinated, for example, is applied. Typical examples of the organic compound constituting the organic probe 22 as above are illustrated in FIG. 8. For the purpose of fluorination of the circumference of the reactive group (—OH), a fluorinated alkyl group such as a trifluoromethyl group (—CF$_3$) or a hexafluoroethyl group (—C$_2$F$_5$) is introduced as a neighboring group of the reactive group into carbon to which the reactive group (—OH) is bonded, for example.

As a structure having a substituted alkyl group described above, there can be cited a 1,1,1,3,3,3-hexafluoro-2-phenyl-2-propanol structure, an α-trifluoromethylbenzyl structure, and so on, which are illustrated in FIG. 8. These structures have an effect of enhancing activity of the reactive group (OH group) by fluorine having a high electronegativity. The reactive group is not limited to the hydroxy group (—OH), and may be an amino group (—NH$_2$) or the like. Further, the neighboring group may be an alkyl group such as a methyl group (—CH$_3$) or an ethyl group (—C$_2$H$_5$).

The organic compound constituting the organic probe 22, as illustrated in an organic compound 1A in FIG. 8, is preferably constituted by an organic compound that has a head portion HS having the above-described reactive group and neighboring group, a base portion BS serving as an installation portion for the graphene layer 26 or the like, and a connecting portion CS connecting the head portion HS and the base portion BS. The head portion HS is preferably an aromatic hydrocarbon group having the reactive group and the neighboring group. The base portion BS is preferably a substituted or unsubstituted polycyclic aromatic hydrocarbon group having a polycyclic structure such as a pyrene ring, an anthracene ring, a naphthacene ring, or a phenanthrene ring, and further, is more preferably a substituted or unsubstituted pyrene group. The connecting portion CS is a single bond or a bivalent group, and may be an alkylene group such as a methylene group or an ethylene group, but is preferably a bivalent organic group having a characteristic group such as an ether bond (—O—), an ester bond (—C(=O)O—), a carbonyl bond (—CO—), an amide bond (—NH—CO—), or an imide bond (—CO—NH—CO—).

The organic probe 22 formed of the aforementioned organic compound (for example, the organic compounds illustrated in FIG. 8) effectively functions against dimethyl methylphosphonate (DMMP) or the like, which is a typical material for a toxic organophosphorus compound, and thus highly accurate detection of the molecule to be detected 2 formed of such a compound molecule is possible. Meanwhile, the organic compounds described above have limited effectiveness against cyanide such as hydrogen cyanide (HCN) or cyanogen chloride (Cl—CN), for example, and it cannot be said that the organic probe 22 functions effectively. The organophosphorus compound has a characteristic bond with phosphorus (P) and oxygen (O), while the cyanide represented by hydrogen cyanide has a significantly different molecular structure. In order to capture such a cyanide molecule by the organic probe 22, it is necessary to devise a structure of an organic compound.

Figure 9:
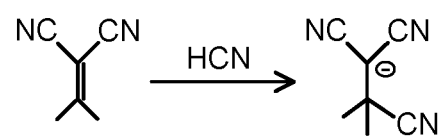
FIG. 9 is a diagram illustrating an example of capturing a cyanide molecule by a dicyanovinyl structure.

In the molecular detection apparatus 1 according to the embodiment, as the organic probe 22 having an interaction with cyanide, an organic compound having a dicyanovinyl structure (CN—(CN—)C=C—) or a coumarin structure (C$_9$H$_6$O$_2$) is used. The dicyanovinyl structure and the coumarin structure each have a double bond site having reactivity with a cyano group (—CN/cyanide ion), and has a good interaction with an electrically negative-biased cyano group (nitrile group) portion of the cyanide. Thereby, it is possible to increase a property of capturing the cyano group. FIG. 9 illustrates the dicyanovinyl structure, and FIG. 10 illustrates the coumarin structure.

FIG. 9 illustrates a reaction example between the dicyanovinyl structure and the cyano group (—CN). The electrically negative-biased cyano group splits a double bond serving as a framework of the dicyanovinyl structure and bonds to one end of carbon which has been generated by splitting. A concrete structure of dicyanovinyl is not necessarily limited, but in view of increasing reactivity with the cyano group (—CN), dicyanovinyl preferably has a structure where two cyano groups are bonded to one of carbon of a carbon-carbon double bond (C=C) serving as the framework of dicyanovinyl. Thereby, a property of splitting the double bond of the dicyanovinyl structure by the cyano group is increased, so that the property of capturing the cyano group can be improved.

Figure 10:
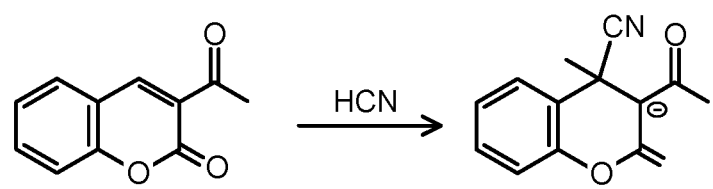
FIG. 10 is a diagram illustrating an example of capturing a cyanide molecule by a coumarin structure.
Figure 11:
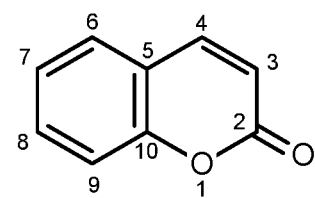
FIG. 11 is a diagram illustrating location numbers of carbons in the coumarin structure.

FIG. 10 illustrates a reaction example between the coumarin structure and the cyano group (—CN). The electrically negative-biased cyano group splits a double bond between carbon at a third location and carbon at a fourth location in the coumarin structure and bonds to one end of the carbon at the fourth location which is generated by splitting. FIG. 11 illustrates location numbers of the carbon in the coumarin structure. In the coumarin structure, the double bond between the carbon at the third location and the carbon at the fourth location illustrated in FIG. 11 is likely to be split by the cyano group. Further, the coumarin structure preferably has an organic group which is bonded to the carbon at the third location and includes a carbonyl group (—C(=O)—). In a case where the coumarin structure has the organic group which includes the carbonyl group, a property of splitting the double bond between the carbon at the third location which is approximate to the carbonyl group and the carbon at the fourth location is increased, so that the cyano group becomes likely to bond to one end of the carbon at the fourth location which is generated by splitting. Therefore, the property of capturing the cyano group can be improved.

By providing the organic compound which has the dicyanovinyl structure or the coumarin structure that has the specific double bond site having the interaction with the cyano group (—CN) as described above to the sensor unit 21 of the detection cell 201 as the organic probe 22, the property of capturing a cyanide compound molecule can be increased. Therefore, it becomes possible to improve a detection sensitivity or a detection accuracy of the cyanide compound molecule by the detector 20. Further, since the organic prove 22 which has the dicyanovinyl structure or the coumarin structure captures the cyanide molecule by the electrically biased cyano group (—CN) acting on the site having the specific double bond structure, higher sensitive detection of the cyanide molecule becomes possible without depending on the surrounding environment or the like. In other words, the detection accuracy of the cyanide molecule can be increased.

Figure 12:
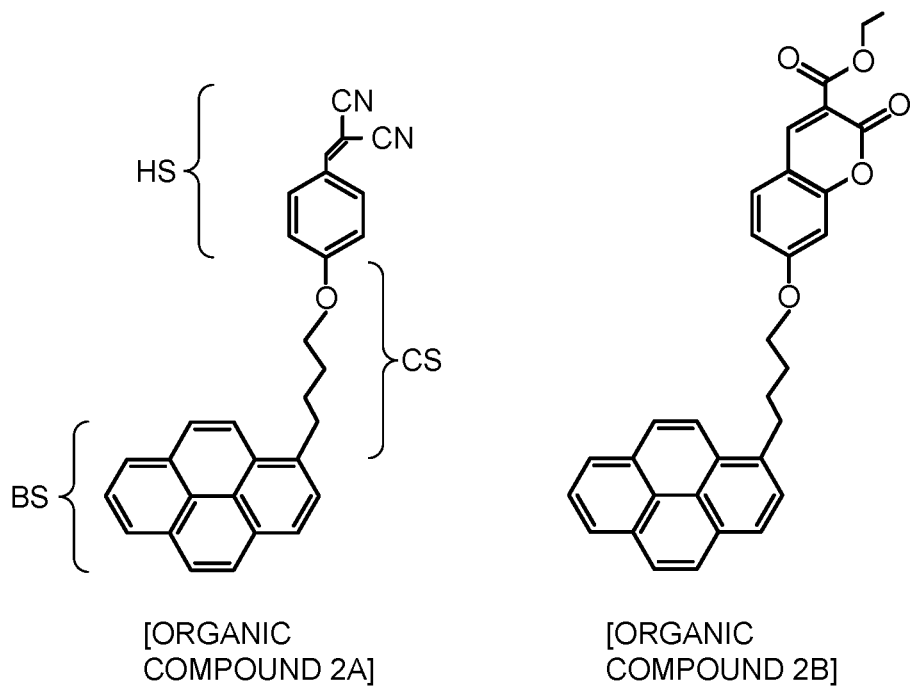
FIG. 12 is a diagram illustrating a second example of the organic compounds used for the organic probes in the molecular detection apparatus of the embodiment.

FIG. 12 illustrates examples of the organic compound that has the dicyanovinyl structure or the coumarin structure, which is used as the organic probe 22. An organic compound 2A has the dicyanovinyl structure, and an organic compound 2B has the coumarin structure. The organic compounds 2A, 2B, similarly to the aforementioned organic compounds 1A to 3C, each have a head portion HS having a reactive group, a base portion BS serving as an installation portion for the graphene layer 26 or the like, and a connecting portion CS connecting the head portion HS and the base portion BS. FIG. 12 illustrates the examples of the organic probe 22, the organic probe 22 that has the dicyanovinyl structure or the coumarin structure being not limited to one formed of the organic compound 2A and 2B illustrated in FIG. 12, and it suffices that the organic probe 22 is formed of an organic compound whose head portion HS has a double bond deriving from the dicyanovinyl structure or the coumarin structure serving as a reacting site with a cyano group and whose base portion BS has an aromatic hydrocarbon group facilitating installation in the graphene layer 26 or the like.

The organic compound 2A has a phenyl group to which a dicyanovinyl group is bonded as the head portion HS, and a double bond of the dicyanovinyl group functions as a reacting site with the cyano group. The head portion HS is not limited to the phenyl group having the dicyanovinyl group and may be another aromatic hydrocarbon group having a dicyanovinyl group. The aromatic hydrocarbon group may have a substituent other than the dicyanovinyl group. As described above, the two cyano groups are preferably bonded to the same carbon of the dicyanovinyl group. The organic compound 2B has an organic group including a carbonyl group as the head portion HS, that is, a coumarin group having "—C(=O)—O—C$_2$H$_5$ group" in FIG. 12, and a double bond between carbon at the third location and carbon at the fourth location of the coumarin group functions as a reaction site with the cyano group. As described above, the coumarin group preferably has an organic group including a carbonyl group bonded to the carbon at the third location.

The base portion BS, similarly to the aforementioned organic compounds 1A to 1C, is preferred to be a substituted or unsubstituted polycyclic aromatic hydrocarbon group having a polycyclic structure such as a pyrene ring, an anthracene ring, a naphthacene ring, or a phenanthrene ring, and further, is more preferably a substituted or unsubstituted pyrene group. The connecting portion CS is a single bond or bivalent organic group, and may be an alkylene group such as a methylene group or an ethylene group, but is preferably a characteristic group such as an ether bond (—O—), an ester bond (—C(=O)O—), a carbonyl bond (—CO—), an amide bond (—NH—CO—), or an imide bond (—CO—NH—CO—), or an organic group such as an alkylene group having the above-described characteristic group. Though the organic compounds 2A, 2B each have a [—C$_4$H$_8$O-group] as the connecting portion CS, the connection portion CS is not necessarily limited thereto.

In the organic compound having the dicyanovinyl structure or the coumarin structure as described above, a bond strength between the organic probe 22 formed of the organic compound as above and the cyanide molecule as the molecule to be detected 2 is different based on a difference in structure of the double bond site serving as the reaction site of the head portion HS and a functional group (a dicyanovinyl group or a coumarin group) having that double bond site or a difference in number of carbon of the bivalent organic group (a hydrocarbon group or the like) as the connection portion CS. Therefore, by providing the organic probes 22 formed of the organic compounds different in bond strength with the cyanide molecule in four detection cells A to D of the detector 20 illustrated in FIG. 5 respectively, for example, strengths of detection signals when the organic probes 22 capture cyanide molecules can be made different. Therefore, the signal patterns based on strength differences of detection signals as illustrated in FIG. 6 and FIG. 7 are obtained, and thereby detection and discrimination of the cyanide molecule is enabled.

The organic probes 22 provided in the plurality of detection cells 201 are not limited to those formed of the organic compounds each having the dicyanovinyl structure or the coumarin structure. It suffices that the organic prove 22 formed of the organic compound having the dicyanovinyl structure or the coumarin structure is provided in at least one of the plurality of detection cells 201. The other detection cells 201 may have the organic probes 22 formed of the organic compounds illustrated in FIG. 8 or organic probes 22 formed of organic compounds 3A, 3B illustrated in FIG. 13 which will be described later. The organic compound 3A illustrated in FIG. 13 has an amino group as a reactive group, while the organic compound 3B does not have a reactive group. The detection cell 201 using the organic compound 3B can be used as a standard cell indicating a reference. Further, detection of the cyanide molecule as the molecule to be detected 2 is not limited to by the pattern recognition method using the plurality of detection cells 201. For example, it is possible to constitute such that an organic probe 22 having a dicyanovinyl structure or a coumarin structure is provided in one detection cell 201 to discriminate a molecule to be detected 2 by a detection signal generated by the organic probe 22 capturing a cyanide molecule.

The detector 20 using the organic probe 22 having the dicyanovinyl structure or the coumarin structure acts effectively in detection of the cyanide molecule as the molecule to be detected 2 as described above. Examples of the cyanide constituting the molecule to be detected 2 include hydrogen cyanide (HCN), cyanogen chloride (Cl—CN), and so on. Further, cyanide such as sodium cyanide (NaCN), potassium cyanide (KCN), silver cyanide (AgCN), or copper cyanide (CuCN) releases hydrogen cyanide (HCN) as a result of reacting with carbon dioxide in the air or heating, so that existence of the cyanide such as sodium cyanide or potassium cyanide can be detected by detection of the hydrogen cyanide (HCN).

According to the molecular detection apparatus 1 of the embodiment, by applying the pattern recognition method for example, selective and higher sensitive detection of a gas molecule having an extremely low concentration in the order of ppt to ppb is enabled. Further, by using the organic probe 22 having the dicyanovinyl structure or the coumarin structure, it is possible to perform highly sensitive detection of the cyanide molecule, which has been hard to be captured by a conventional organic probe, without depending on the environment or the like where the molecule to be detected 2 exists. Thus, highly accurate detection of a gas molecule such as a cyanide molecule becomes possible. Further, by increasing a detection sensitivity and a detection accuracy by the detector 20 and the discriminator 30, miniaturization of the molecular detection apparatus 1 is enabled. Accordingly, it is possible to provide the molecular detection apparatus 1 where the portability and the detection accuracy are both enabled. The molecular detection apparatus 1 as stated above effectively exerts the functions thereof at various sites such as a site of environmental measurement of a water quality or the atmosphere, a site where a toxic materials such as cyanide is diffused by disaster, or a site where an act of terrorism has occurred.

Figure 14:
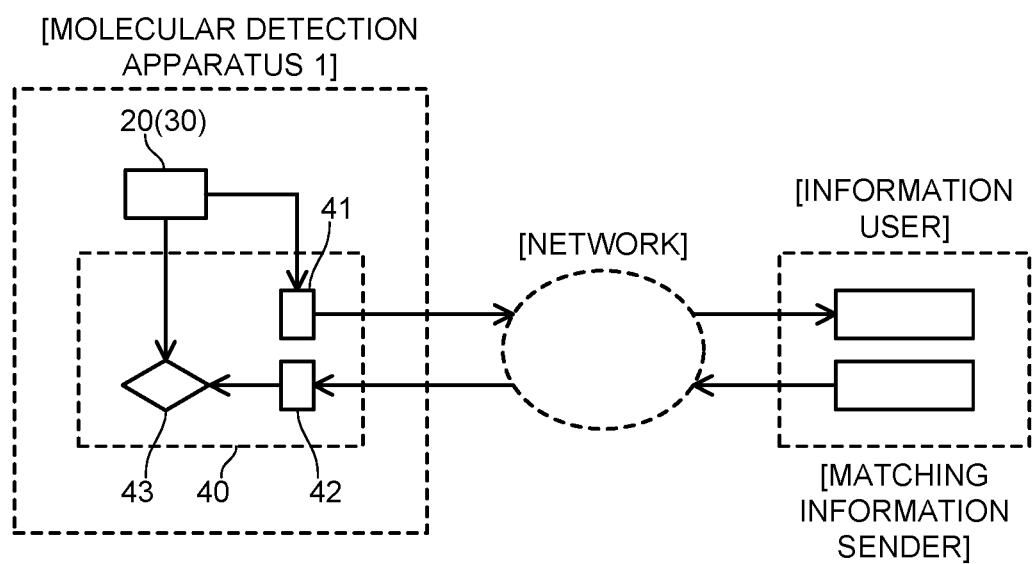
FIG. 14 is a diagram illustrating an information processing unit in the molecular detection apparatus of the embodiment.

Detection and discrimination results of the molecule to be detected 2 obtained in the molecular detection apparatus 1 of the embodiment may be used by being transmitted via an information network. FIG. 14 illustrates a configuration example of a molecular detection apparatus 1 to which is attached or inside which is provided an information processing unit 40 having a function of transmitting the detection information of the molecule to be detected 2 via the information network and a function of matching the detection information with reference information acquired from the information network. The information processing unit 40 includes an information transmitting unit 41 which transmits detection information of the molecule to be detected 2, an information receiving unit 42 which receives reference information, and an information matching unit 43 which matches the detection information with the reference information. The information processing unit 40 may have only one of information matching functions including an information transmitting function and an information receiving function.

The detection information of the molecule to be detected 2 is transmitted from the information transmitting unit 41 to an information user via the network. For matching of the detection information of the molecule to be detected 2 with existing reference information, the reference information is acquired by the information receiving unit 42 via the network. The acquired reference information is matched with the detection information by the information matching unit 43. By acquiring information from the external network to then perform matching, a function of carrying much information for analysis can be replaced by an external portion, so that the molecular detection apparatus 1 can be further miniaturized to thereby increase portability. Besides, use of a network transmission means also enables immediate acquisition of a new signal pattern in the pattern recognition method. A reception side of the information can take a next action based on the above information. The molecular detection apparatus 1 can be used in such a way that molecular detection apparatuses 1 having portability are disposed in various places, obtained data being collected from the respective places to be analyzed, to be made use of in evacuation guide in an abnormal situation or the like. Combining the network and the molecular detection apparatus 1 creates many usages which have been conventionally unavailable, to thereby improve an industrial value.

EXAMPLES

Next, concrete examples and evaluation results thereof will be described.

Example 1

First, a detection element in which a GFET and an organic probe are combined is prepared as follows. A graphene layer is formed by transferring graphite onto a substrate by an exfoliation method or by growing graphene on a surface of a metal by using a chemical vapor deposition method (CVD). A single layer or a plurality of layers of graphene grown on the surface of the metal are transferred onto a polymer film, and the resultant polymer film is transferred again onto a desired semiconductor substrate for field effect transistor (FET) fabrication. For example, graphene is formed on a surface of a copper foil by CVD with flowing of a methane gas under a condition of approximately 1000° C.

Next, a polymethyl methacrylate film is applied at 4000 rpm by using a spin coating method, and the copper foil film of the opposite surface is etched with an ammonium persulfate 0.1M solution, and thereby a graphene film floating in the solution is recovered. By doing this, the graphene film is transferred onto the polymethyl methacrylate film side. A surface thereof is sufficiently cleaned, and then the graphene film is transferred onto a silicon substrate again. The redundant polymethyl methacrylate film is dissolved with acetone to be removed. A resist is applied onto the graphene transferred onto the silicon substrate to undergo patterning, and a pattern with a 10 μm electrode interval is formed by oxygen plasma. Electrodes are deposited to form an FET structure on which a source electrode and a drain electrode are provided. The graphene is disposed on an oxide film formed on the surface of the silicon substrate and an FET type sensor structure is formed in which the graphene is sandwiched between the source electrode and the drain electrode and the silicon substrate side is set as the gate electrode.

Figure 13:
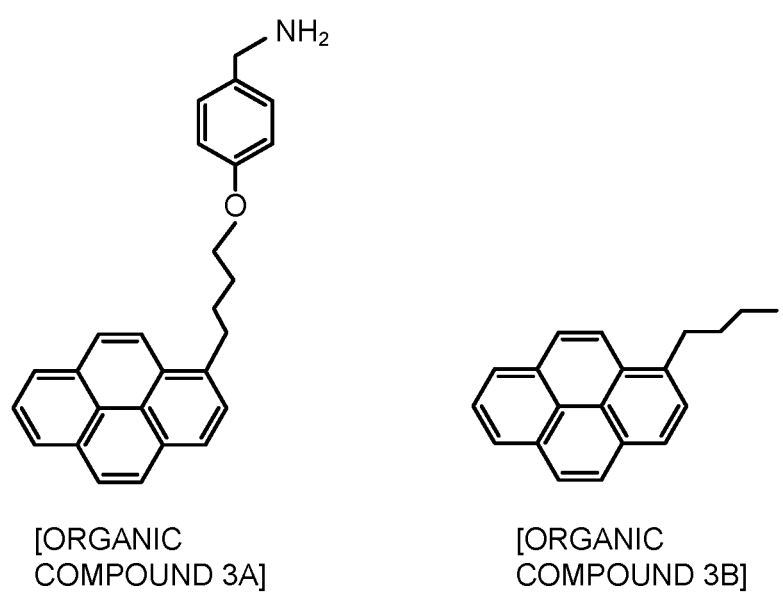
FIG. 13 is a diagram illustrating a third example of the organic compounds used for the organic probes in the molecular detection apparatus of the embodiment.

Next, an organic probe is provided on the surface of the graphene. The organic probe is installed in a manner that an organic compound is dissolved in a methanol solution with a concentration of 10 nM and a graphene sensor surface is immersed in the resultant solution for several minutes. For the organic probe, the organic compounds 2A, 2B illustrated in FIG. 12 and the organic compounds 3A, 3B illustrated in FIG. 13 are used. In Example 1, as illustrated in FIG. 5, four detection cells A to D are provided on a detection surface of a detector, and there are installed the organic compound 2A for the detection cell A, the organic compound 2B for the detection cell B, the organic compound 3A for the detection cell C, and the organic compound 3B for the detection cell D, respectively, as the organic probes. As described above, the organic compounds 2A, 2B, 3A, 3B are each different in bond strength with a molecule to be detected (cyanide molecule).

Next, hydrogen cyanide (HCN) is prepared as the molecule to be detected. With regard to the molecule to be detected, its vapor is diluted with a nitrogen gas to have a concentration of about 5 ppb, and a resultant diluted gas is sent to the detector. The molecules to be detected are captured by the organic probes of the detection cells A to D, respectively. Since the organic probes of the detection cells A to D are each different in bond strength with the molecule to be detected, signals detected by gate electrodes are also each different. Results detected in the detection cells A to D are sent to a discriminator which performs a signal processing, to be converted into strengths. The detection results are outputted in a form of relative strength indication as illustrated in FIG. 6. In the detection results illustrated in FIG. 6, the strength of the detection signal in the detection cell D, which is lower than those in the other detection cells by two digits or more, is illustrated as "0" (zero). The detection results of the molecules to be detected indicate signal patterns based on signal strength differences of the detection cells A to D, and it is understood that discrimination of the molecules to be detected based on such signal patterns enables selective and higher sensitive detection of the molecule to be detected 2 having an extremely low concentration in the order of ppb.

Example 2

A detector is constituted similarly to the Example 1 by using the organic compounds 2A, 2B illustrated in FIG. 12 and the organic compounds 3A, 3B illustrated in FIG. 13 as organic probes provided on a surface of graphene of a GFET sensor fabricated similarly to the Example 1. A molecule to be detected (hydrogen cyanide) is detected by using the detector as above. On this occasion, a water molecule is also mixed as well as the molecule to be detected (hydrogen cyanide). In other words, vapor of the molecule to be detected (hydrogen cyanide) is diluted with a nitrogen gas containing water vapor of 100 ppb so as to have a concentration of about 5 ppb and sent to the detector. Detection results of the molecules to be detected are illustrated in FIG. 7. As illustrated in FIG. 7, the detection results of the molecules to be detected indicate signal patterns based on signal strength differences of the detection cells A to D, and it is understood that discrimination of the molecules to be detected based on such signal patterns enables selective and higher sensitive detection of the molecule to be detected having an extremely low concentration in the order of ppb.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The inventions described in the accompanying claims and their equivalents are intended to cover such forms or modifications as would fall within the scope and spirit of the inventions.

What is claimed is:

1. A molecular detection apparatus, comprising:
a collection unit including a collection port collecting a detection target gas containing a molecule to be detected, and an outlet port for the molecule to be detected;
a detector comprising a first detection cell disposed to face the output port of the collection unit, which includes a first sensor unit including a field effect transistor having a graphene layer, and a source electrode and a drain electrode connected to the graphene layer, and a first organic probe provided in the graphene layer of the first sensor unit, the first organic probe including a dicyanovinyl structure or a coumarin structure which includes a double bond site capturing the molecule collected in the collection unit; and
a discriminator configured to discriminate the molecule based on a detection signal generated from the first sensor unit by the molecule being captured by the first organic probe of the first detection cell.

2. The apparatus according to claim 1, wherein the molecule includes a cyanide molecule.

3. The apparatus according to claim 1, wherein the dicyanovinyl structure in the first organic probe has two cyano groups bonded to the same carbon in a double bond serving as a framework of dicyanovinyl.

4. The apparatus according to claim 1, wherein the coumarin structure in the first organic probe has an organic group containing a carbonyl group which is bonded to a third location of carbon in coumarin, wherein when a location of oxygen in the coumarin is a first location, the third location of carbon is a carbon existing thirdly from the first location of oxygen.

5. The apparatus according to claim 1, wherein:
the detector further comprises a second detection cell including a second sensor unit including a field effect transistor including a graphene layer, and a source electrode and a drain electrode connected to the graphene layer, and a second organic probe provided in the graphene layer of the second sensor unit;
the second organic probe is an organic probe of the same or different in kind from the first organic probe, and has bond strength with the molecule which is different from the first organic probe; and
the discriminator is configured to discriminate the molecule by a signal pattern based on a difference of signal strengths between the detection signals generated by the molecules being captured by the first and second organic probes of the first and second detection cells.

6. The apparatus according to claim 1, wherein the first organic probe is formed of an organic compound which has a head portion having the dicyanovinyl structure or the coumarin structure, a base portion having a polycyclic aromatic hydrocarbon group, and a connecting portion having a single bond or a bivalent organic group bonding the head portion and the base portion.

7. A molecular detection method, comprising:
collecting a detection target gas containing a molecule to be detected;
capturing the collected molecule by a first organic probe which is provided in a first sensor unit and includes a dicyanovinyl structure or a coumarin structure, wherein the first sensor unit includes a field effect transistor including a graphene layer, and a source electrode and a drain electrode connected to the graphene layer, and the first organic probe is provided in the graphene layer of the first sensor unit; and
detecting and discriminating the molecule based on a detection signal generated from the sensor unit by the molecule being captured by the first organic probe.

8. The method according to claim 7, wherein a cyanide molecule is detected as the molecule.

9. The method according to claim 7, wherein the dicyanovinyl structure in the first organic probe has two cyano groups bonded to the same carbon in a double bond serving as a framework of dicyanovinyl.

10. The method according to claim 7, wherein the coumarin structure in the first organic probe has an organic group including a carbonyl group which is bonded to a third location of carbon in coumarin, wherein when a location of oxygen in the coumarin is a first location, the third location of carbon is a carbon existing thirdly from the first location of oxygen.

11. The method according to claim 7, wherein:
the molecule is captured by a organic probe and a second organic probe which is provided in a second sensor unit, wherein the second sensor unit includes a field effect transistor including a graphene layer, and a source electrode and a drain electrode connected to the graphene layer, and the second organic probe is provided in the graphene layer of the second sensor unit, and is an organic probe of the same or different in kind from the first organic probe, and has bond strength with the molecule which is different from the first organic probe; and
the molecule is discriminated by a signal pattern based on a difference of signal strengths between the detection signals generated by the molecules being captured by the first and second organic probes.

12. The method according to claim 7, wherein the first organic probe is formed of an organic compound which has a head portion having the dicyanovinyl structure or the coumarin structure, a base portion having a polycyclic aromatic hydrocarbon group, and a connecting portion having a single bond or a bivalent organic group bonding the head portion and the base portion.

* * * * *